United States Patent
Lee et al.

(10) Patent No.: US 10,417,389 B2
(45) Date of Patent: Sep. 17, 2019

(54) APPLICATION DEVELOPMENT SYSTEM FOR MEDICAL PUMPS

(71) Applicant: Zyno Medical, LLC., Natick, MA (US)

(72) Inventors: Chao Young Lee, Weston, MA (US); Mei Zhang, Sharon, MA (US); James Zhimin Yan, West Roxbury, MA (US)

(73) Assignee: Zyno Medical, LLC, Natick, MA (US)

( * ) Notice: Subject to any disclaimer, the term of this patent is extended or adjusted under 35 U.S.C. 154(b) by 302 days.

(21) Appl. No.: 14/959,622

(22) Filed: Dec. 4, 2015

(65) Prior Publication Data

US 2017/0161460 A1    Jun. 8, 2017

(51) Int. Cl.
*A61M 5/142*    (2006.01)
*G06F 19/00*    (2018.01)

(52) U.S. Cl.
CPC ................. *G06F 19/3468* (2013.01)

(58) Field of Classification Search
CPC .......................................... A61M 2005/14208
USPC ............................................................ 604/151
See application file for complete search history.

(56) References Cited

U.S. PATENT DOCUMENTS

| | | | |
|---|---|---|---|
| 2003/0171846 A1* | 9/2003 | Murray, IV | B25J 9/161 700/245 |
| 2007/0124002 A1* | 5/2007 | Estes | A61M 5/172 700/20 |
| 2008/0126969 A1* | 5/2008 | Blomquist | A61M 5/142 715/771 |
| 2009/0099498 A1* | 4/2009 | Demers | A61M 1/106 604/6.09 |
| 2015/0081894 A1* | 3/2015 | Blomquist | G06F 19/3456 709/224 |
| 2015/0141955 A1* | 5/2015 | Ruchti | G06F 19/3468 604/506 |
| 2016/0008634 A1* | 1/2016 | Payne | A61N 7/00 600/411 |
| 2016/0228633 A1* | 8/2016 | Welsch | A61M 5/142 |

* cited by examiner

*Primary Examiner* — Min Huang
(74) *Attorney, Agent, or Firm* — Boyle Frederickson S.C.

(57) ABSTRACT

An application authoring tool and application program system for medical pumps provides each pump with a standardized hardware interface abstracting the hardware and tasks done by the pump in order to provide a uniform interface for application programmers across different pump types. The standardized interface may translate hardware communication with hardware on different machines, do hardware signal range checking, and handle routine but detailed hardware tasks such as error reporting. A system for installing multiple applications on pumps allows a flexible trade-off between reducing pump programming time by loading specialized application programs and preserving pump flexibility by allowing the user to select among multiple applications.

12 Claims, 4 Drawing Sheets

APPLICATION DEVELOPMENT SYSTEM FOR MEDICAL PUMPS

BACKGROUND OF THE INVENTION

The present invention relates to medical pumps and in particular to a system for facilitating development of custom applications for medical pump hardware.

Medical pumps, such as syringe pumps or peristaltic infusion pumps, are known for computer-controlled delivery of medication or contrast agents (henceforth medicaments) to patients over a period of time. Typically the medicament is delivered in a syringe (for a syringe pump) or a flexible bag (for peristaltic infusion pump, or ambulatory pump) that may be connected to an IV line and attached to a needle inserted into the patient. When a nurse or other healthcare professional ministering to the patient receives the medicament, the healthcare professional reviews the medicament description for correctness and enters the desired dose and rate into the pump. Other pump parameters such as alarm limits and the like may also be programmed at this time. The syringe or IV line must then be mechanically connected to the pump mechanism, the needle introduced into the patient, and the mechanism activated to begin pumping.

Medical pumps provide a platform for the controlled delivery of medicaments and as such are potentially useful in a wide variety of different medical procedures.

The use of medical pumps is limited by the availability of appropriate control software and the complexity of entering operational parameters for more than a simple medicament delivery schedule (e.g., flow rate and total volume). Some medical pump applications are common enough to justify the manufacture of specialized pumps for particular procedures, hut this approach, which results in many specialized pumps, has significant drawbacks to organizations which must manage multiple pumps for a wide variety of conditions. These organizations, including hospital and outpatient healthcare provider services, often operate many different pump designs and versions.

SUMMARY OF THE INVENTION

The present invention provides a medical pump that facilitates the development of third-party application programs for medical pumps in a manner roughly analogous to the development of application programs for smart devices such as cell phones and tablets. The medical pump provides both an application loader program that simplifies the receipt and display of developed application programs, and an operating system that presents abstractions of the hardware of a medical pump to permit cross-platform development encouraging the development of application program. Using this system, an individual healthcare provider may develop and/or download one or more application programs that may be certified to operate the pump correctly. Selecting a specialized application program avoids the need for complex reconfiguration of a "one-size-fits-all" pump control program with multiple manually entered parameters that vary from pump to pump.

In one embodiment, the invention provides a medical pump having a housing holding hardware elements including: (i) an electrical pump for receiving an IV line controlling a flow of liquid medicament therethrough; (ii) one or more sensors for sensing pump conditions; and (iii) an electronic user interface providing a display and keyboard. An electronic memory holds an operating system and application loader program and an electronic computer communicating with the hardware dements and electronic memory and executing the operating system and application loader program to: (1) receive one or more application programs for loading into the electronic memory; (2) display representations of the application programs on the display for executing by user input to the keyboard; and (3) communicate between the application program and the hardware elements through the operating system, the latter providing a set of standardized hardware interfaces to the hardware elements providing identical abstractions of features of multiple different hardware elements among different medical pumps.

It is thus a feature of at least one embodiment of the invention to greatly expand the pool of available software for medical pumps in order to promote application programs that can better leverage the scarce time of healthcare professionals.

The standardized hardware interfaces may include a standard session interface exchanging information between an application program and the hardware elements to coordinate among a pump and, at least one sensor for sensing fluid flow to provide a patient treatment session for an individual patient.

It is thus a feature of at least one embodiment of the invention to provide standardized interfaces that can combine multiple hardware elements and in particular to provide a standardized hardware interface relevant to the primary functions of medical pumps to simplify the development of application programs.

The session interface may include a standard error event exchanging information between an application program and the hardware elements to coordinate a stopping of the pump in the event of a predetermined error condition related to the flow of medicament determined by a sensor.

It is thus a feature of at least one embodiment of the invention to free the application, programmer from the necessary analysis of possible error conditions such as may require specialized expertise.

The application loader program may operate to load application programs into the electronic memory only if the application programs include embedded authentication data.

It is thus a feature of at least one embodiment of the invention to provide a balance between improving the freedom to develop application programs for pumps and needing to ensure safety in the operation of the pumps by the application programs. The authentication data permits a certificate process to be implemented.

The application loader program may operate to load multiple application programs and display the multiple application programs in a hierarchical menu structure on the display, each application program independently operable to control the medical pump for patient treatment.

It is thus a feature of at least one embodiment of the invention to permit individual pumps to be rapidly programmed by selecting among application programs.

The medical pump may include a wireless receiver and the application loader program may receive application programs wirelessly.

It is thus a feature of at least one embodiment of the invention to allow central coordination of multiple pumps at a facility through a wireless downloading process.

The application loader program may compare the standardized hardware interfaces used by the application program to standardize hardware interfaces available on the medical pump before receiving an application program.

It is thus a feature of at least one embodiment of the invention to permit the unencumbered dissemination of advanced applicable programs without concern even if those programs may not be universally able to operate on legacy medical pumps.

The standardized hardware interface may provide a plurality of software objects associated with the hardware elements, the objects providing object properties having values describing operation of the hardware elements, object methods having sequences of steps for controlling the hardware elements, and object events having test conditions receiving information from the hardware elements to trigger outputs to the application programs.

It is thus a feature of at least one embodiment of the invention to employ an object model for generation of the standard interface such as permits the use of advanced programming languages.

The software objects may include: a pump object, at least one sensor object, a data logging object, a display object, a keyboard object; and an error object.

It is thus a feature of at least one embodiment of the invention to provide fundamental building blocks for medical pump applications.

The data logger object may record the digital signature of the application program.

It is thus a feature of at least one embodiment of the invention to expand the development of application programs while preserving traceability necessary for medical devices.

The software objects may include a session object coordinating the electrical pump and the one or more sensors according to a timer.

it is thus a feature of at least one embodiment of the invention to provide a multi-hardware abstraction for the basic operation of the medical pump greatly simplifying the development of application programs.

The standardized hardware interface may limit the operating conditions of associated hardware elements independently of data received by the application programs.

It is thus a feature of at least one embodiment of the invention to use the standardized interface to free the application programmer from concern about the operating parameters of a variety of different types of hardware.

The application loader program may further operate to remove one or more application programs from the electronic memory.

It is thus a feature of at least one embodiment of the invention to simplify the addition and removal of application programs so that the application program suite may be adjusted by particular institutions to meet their needs.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

DETAILED DESCRIPTION OF THE PREFERRED EMBODIMENT

Figure 1:
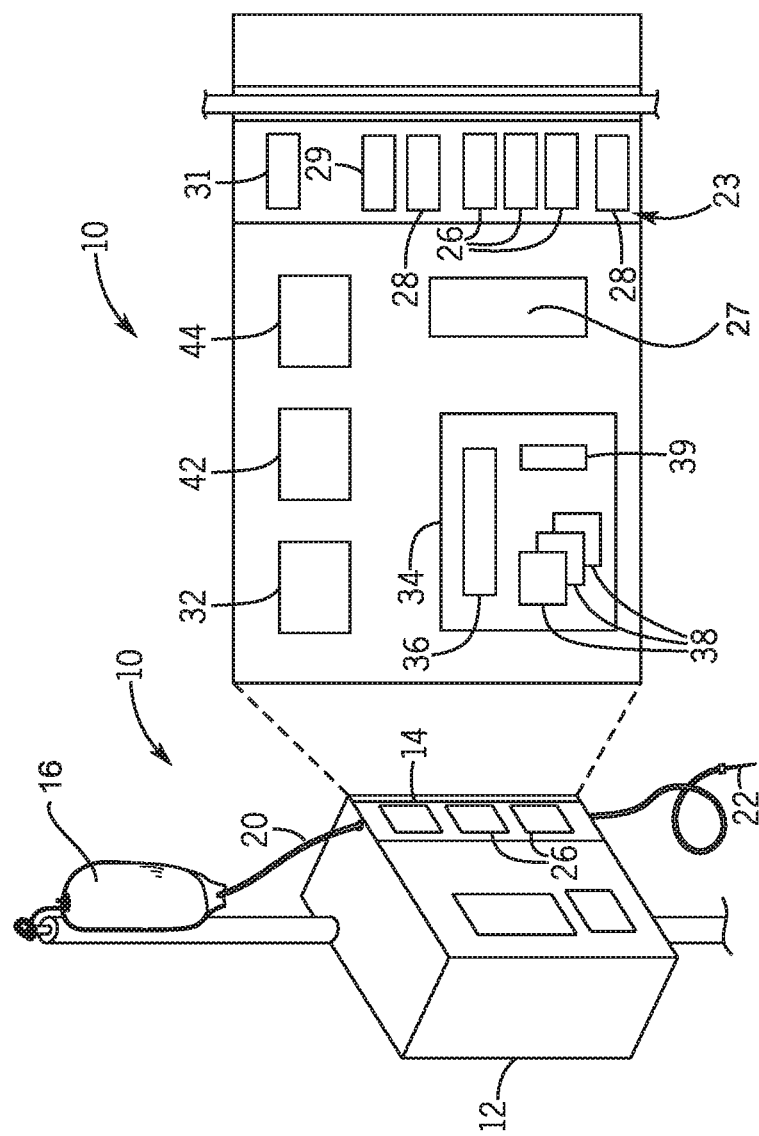
FIG. 1 is a simplified perspective view of a medical pump employing the system of the present invention and showing an expanded block diagram of its constituent hardware elements as well as memory holding an operating system, an application loader program and one or more application programs.

Referring now to FIG. 1, an infusion pump 10 may provide for a housing 12 providing a pump compartment 14 through which an IV line 20 may be threaded. The IV line 20 may communicate from an IV bag 16 to a needle 22 or similar connection to the patient.

The pump compartment 14 may provide a pump 23 exposing peristaltic pump elements 26 controlled by a pump element actuator 27 and through which the IV line 20 may be threaded for controllably pumping, liquid therethrough according to techniques understood in the art. Generally, each peristaltic pump element 26 may compress a short successive segment of the IV line 20 (for example, according to two or more square wave pulse pulses shifted by 90° with respect to one another) to pump fluid along the IV line 20, A section of the IV line 20 fitting within the pump elements 26 may be specially constructed of a highly flexible silicone material. For example, the IV line 20 may be a highly compliant material that may be sterilizable and is, preferably, non-Pyrogenic, non-DEHP and latex free. One such material is silicone rubber which provides for high compliance as will be desired for pressure sensing to be described below. Another example is non-DEHP PVC material.

Also positioned within the pump compartment 14 are one or more pressure sensors 28 providing for IV line pressure before and after the pump elements 26 and before the needle 22. The sensors 28 are placed adjacent to the IV line 20 for the detection of occlusion as is generally understood in the art. A bubble sensor 29 may also be provided adjacent to the IV line 20 for the detection of bubbles within the IV line 20, and an IV line presence sensor 31 may be positioned in the pump compartment 14 for determining whether the IV line 20 is properly seated within the pump compartment 14 and received by the sensors 28, 31 and peristaltic pump elements 26.

Referring still to FIG. 1, the pump 10 may include a processor 32 (which may be a microcontroller based system) having a memory 34. The memory 34 may hold a stored operating system program 36 controlling operation of, the pump 10 according to one or more control application programs 38, the latter of which control volume and rate of desired drug delivery through the IV line 20 as will be discussed below. An application loader program 39 is also held in the memory 34 and is used to manage and control the application programs 38 as will be discussed below.

In general, the processor 32 may execute the application programs 38 which communicate through a standardized interface (as will be discussed below) contained in the operating system program 36 to connect with various hardware elements of the infusion pump 10 as mediated by the processor 32. For example, the application programs 38 in this manner may control the pump dements 26 in the pump compartment 14 to provide the desired dose and delivery rate to the patient, for example, by providing successive compressing elements for peristaltically moving fluid through the IV line 20. Application programs 38 may further communicate with the pressure sensors 28 of the present invention for receiving a signal therefrom to monitor pressure in the IV line 20 for detection of upstream or downstream obstruction of the IV line 20 by monitoring a time signature of the pressure waveform from the sensor 28. Application programs 38 may also communicate with the bubble sensor 29 and IV line presence sensor 31 to detect possible error conditions under which operation of the pump should cease.

The application programs 38 may also communicate via processor 32 with a display 41, for example, an LCD display, for displaying various programming and operating parameters and a switch array/keyboard 40 for inputting data, for example, for programming or initiating or stopping of the pumping action. It will be appreciated that any keyboard may be used for the keyboard 40 including, for example, a touchscreen. In addition the processor 32 may communicate with the wireless transceiver 42 and RFID tag reader 44, the latter for confirming patient or user identities or other local information and the former used for downloading application programs 38 or communicating information to a remote site.

Figure 2:
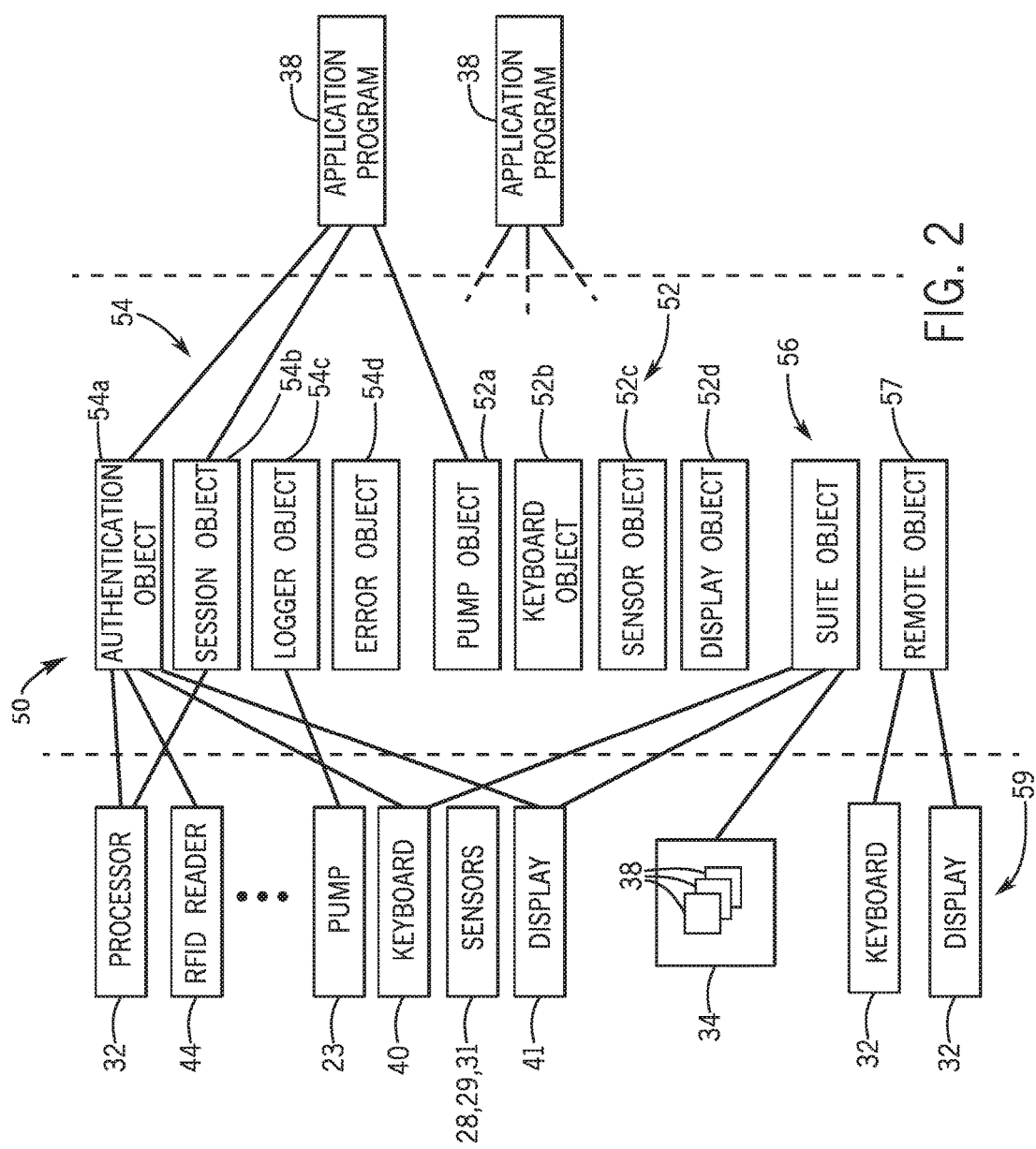
FIG. 2 is an interface diagram showing the inter-positioning of a standardized software-implemented hardware interface between application programs run on the pump of FIG. 1 and the hardware elements of FIG. 1.

Referring now to FIG. 2, the present invention contemplates that the hardware of the pump 10 will be abstracted by a standard hardware interface 50 that will greatly simplify the development of application programs 38 for the pump 10 permitting a flexible implementation of specialized pumps for particular medical applications without dedicating those pumps to that medical application. The process of producing a specialized pump effectively moves labor and effort from medical practitioners in programming a variety of pumps to the application program running on the pump to minimize the necessary data entry and to provide a more uniform user experience over variety of different hardware types. While in this process, the specialized application program 38 reduces the flexibility of the pump, this reduction in flexibility reduces the necessary programming by the operator needed in the general-purpose pump. Ultimately flexibility of the pumps is restored by the ability to select among multiple specialized applications.

As depicted in FIG. 2 the standard hardware interface 50 simplifies and standardizes the process of developing application programs 38 for different pumps 10 by presenting the application programmer with the appearance of standardized and simplified hardware to "hardware objects". The standardized hardware interface 50 may also provides "task objects" which do not have a simple one-to-one correlation with hardware but that present atomistic tasks that the application programmer will wish to accomplish using combinations of hardware and software. The standardized hardware interface 50 may also provide similar objects for managing the application programs 38; in this regard, the standard hardware interface 50 will generally include physical object interfaces 52, task interfaces 54, and application management interfaces 56 which may in one embodiment be expressed by means of software objects that can be instantiated by the application programs as needed. The software objects provide methods (that is, functions associated with the objects that can be called by the application programs 38), events (that is, automatic outputs from the objects to the application programs 38 providing real-time information, for example, error conditions), and properties (that is, variable values that provide conditions for methods and events).

For example, the hardware objects 52 may include a pump object 52a uniquely associated with the pump 23, a keyboard object 52b uniquely associated with the keyboard 40, sensor objects 52c associated with a particular sensor 28, 29, or 31, and a display object 52d associate with the display 41. These hardware objects 52 will each include several standard functions. First, they will perform a range checking to make sure that the commands provided through the object 52 from the application program 38 to a hardware element, in the form of a command, are within the range of the hardware. So, for example, a flow delivery rate requested by an application program 38 for pump 23 will be checked to ensure that it can be implemented by the particular hardware of the pump 23. If not, this command will be automatically trapped as an error communicated from an error object to he discussed below, or modified to fit within the operating range of the hardware. This latter situation illustrates a second standard function provided by objects 52 which is to translate, to the extent possible, commands received from application programs 38 into usable ranges for the specific hardware of the pump 10 and, in the opposite direction, to translate signals received from hardware of the pump 10 into a standard set of ranges understood by the all application programs 38. Thus, for example, different sensors 28 may provide for a different range of voltage outputs which objects 52c can translate into a common pressure range.

The hardware objects 52 can also encapsulate standard functions usable with the hardware, for example, ramping up the pump speed and ramping down the pump speed according to set parameters, checking for pump errors, tom example, pump stall conditions or overheating, and providing the necessary events, for example, error events.

The task objects 54 generally provide interfaces with multiple hardware elements in useful combinations tailored to medical pumping applications. For example, the task interfaces 54 may include an authentication task object 54a providing method events and properties related to authenticating the patient, the pump settings, the medicament, and the supervising healthcare professional. Authentication methods may include receiving authorization codes from a user (if desired for confirmation of the patient), for example, through the REED tag reader 44, determining that current application program 38 is up to date, for example, determined through wireless transceiver 42, determining that the IV line 20 is properly installed with the door closed using sensor 31, and determining that the proper medicament has been loaded, for example, as detected by a tag read by RFID tag reader 44.

A session object 54b may provide for coordination of various hardware elements to provide a drug delivery session, for example, having a duration, a flow rate, and total flow volume. The session object 54b differs from the pump object 52 in that it may include communication with timer objects, for example, making use of hardware timers in the processor 32 as well as the sensors (for example, flow sensors 28) and control of the pump 23.

The invention may also provide a data logger object 54c that provides real-time logging of the operation of the pump 10 including values from the sensors and pump synchronized to time from the processor 32. The data logger object 54c may also log errors, as will be discussed below, and the identity of the application programs 38 for the purpose of identifying possible failures that may be linked to application programs 38 for the purpose of quality improvement.

As noted above, error task object 54d may provide for an object that handles the detection and reporting of errors in the operation of the pump 10. Importantly, the error task object 54d may generate a variety of predefined events related to hardware or operating errors that can be predefined to relieve the application programmer of this task and to eliminate the need for the application programmer to understand the various hardware error conditions that may result from certain methods. The error task object 54d may provide for standard reporting through the display 41 and wireless transceiver 42.

As with the other objects, the application programs 38 may make use of this object 54d by instantiating it, setting its properties, and trapping its events and invoking its methods as is generally understood in the art.

The invention may also include a suite object 56 that helps manage multiple application programs 38 by communicating with the application loader program 39 to register and display various application programs 38. The suite object 56 may be invoked by the user, as well as communicate with the application programs 38 to provide for management of multiple application programs 38 permitting the user to select and load individual application programs 38 from a set of application programs 38 held in the pump 10 for execution by the pump 10. By selecting application program 38, pre-defined and specialized pump operations dictated by the loaded application program 38 can be obtained.

Generally the suite object 56 will also operate to display the available application programs 38 in hierarchies and be labelled to identify each application program 38 on the display 41 or the like. In use, each pump 10 may display a range of different application programs 38 in a tree structure listing their purpose and application so that the user may quickly identify a needed application and invoke that application for a particular medical procedure. The application programs 38 when loaded may invoke the suite object 56 to install their identifications and an icon or the like.

The suite object 56 may also control the launching of application programs 38 to be limited to particular users through, for example, authorization codes, and may further control the visibility of different application programs 38 in the hierarchy according to the user's authorization level. Generally the suite object 56 allows different pumps 10 to present different application programs 38, for example, to limit some pumps to particular applications. In this regard, suite object 56 from different pumps 10 may communicate using the wireless transceiver 42 to facilitate an institution-wide management of various application programs 38 on different pumps 10 so that different pumps 10 may present different application programs 38.

A remote object 76 may also be provided providing the ability of a programmer to make use of a remote communication protocol (for example, Bluetooth or other wireless protocols) to communicate with a remote user interface such as a cell phone or desktop computer and in this way tap into the functional resources 59 of that remote user interface when those features are not available in the pump 10. For example, the remote user interface may provide resources 59, such as a superior screen or keyboard or the ability to be mobile. In this way, legacy pumps 10 or a wider variety of pumps 12 may work with application programs that require more sophisticated user interfaces that may only be available on some pumps or relatively high-end or new pumps 12.

Figure 3:
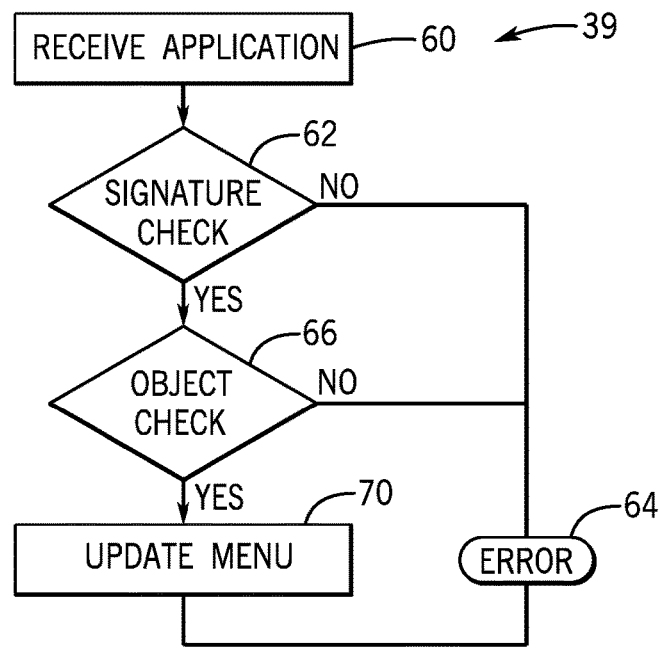
FIG. 3 is a simplified flowchart of the application loader program for loading application programs into the pump of FIG. 1.

Referring now to FIG. 3, the application loader program 39 will generally receive application programs 38, for example, through the wireless transceiver 42 as indicated by process block 60. At decision block 62, each application program 38 is checked see that it is properly digitally signed either or both by the pump manufacturer who authenticates the proper operation of each application program 38 and the institution (such as a hospital or other healthcare organization) who may want to lock out certain application programs 38 from their suite of assets. The digital signature may, for example, use public-key encryption to reduce the ability of counterfeiting of such signatures.

if the signature on an application program 38 being loaded by the application loader program 39 is not correct, an error condition is invoked and the user informed by error process block 64 of that error. This error condition may be displayed locally at the pump 10 and/or at the remote site controlling the downloading.

At decision block 66, if the digital signature order is correct, decision block 62 checks to see that the necessary objects needed by the application program 38 are available in the given pump 10. It should be noted that the necessary objects may be available even if the physical hardware is not available to the extent that existing physical hardware can implement the function of the missing hardware element through an object. So for example, the application program 38 may require an IV line 20 presence sensor which is not available in the pump 10 but whose function may be implemented by the pressure sensor which detects the lack of an IV line through a zero pressure level. So long as the object is available, the application program 38 can work whether or not the particular underlying hardware is available.

If the needed object is not available, as determined at decision block 66, the application loader program 39 proceeds to the error process block 64. Otherwise at process block 70, the hierarchy of application programs 38 displayed on the display 48 is updated allowing user to select the new application program 38 from among other application programs 38 on the pump 10 using the suite object 56.

Figure 4:
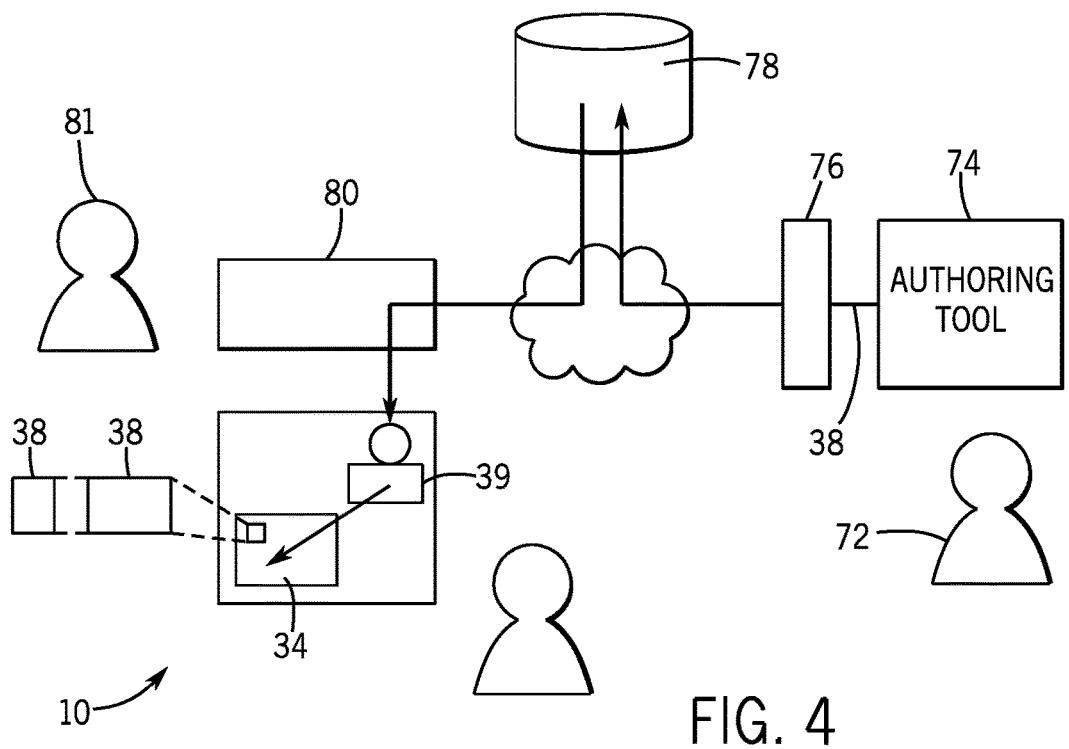
FIG. 4 is a system diagram, of a process of generating and loading application programs into a set of medical pumps.

Referring now to FIG. 4, the invention contemplates that it will encourage a significant increase in the available software for given pump hardware. In that process an application programmer 72 may prepare applications using an application authoring program 74, for example, being a C++compiler, having a library with the necessary objects described above. The resulting application program 38 may then be validated, for example, by the manufacturer as shown by validation block 76 and if properly validated stored in a content repository 78 for use by pump owners. An institution management program 80 may be used by hospital personnel 81 or the like to disseminate particular application programs 38 to particular pumps 10 wherein the application programs 38 are received through the application loader program 39 and stored in memory 34 for selection by a user 82. The invention contemplates that in this manner, the mechanisms of an "App Store" may be used to encourage improved software and software variety for medical devices using this technique.

Figure 5:
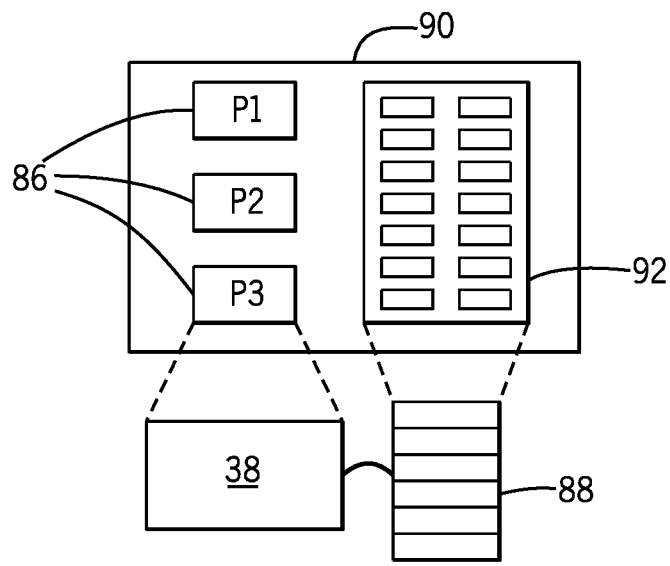
FIG. 5 is a screen display presenting a user with simple procedure alternatives greatly simplifying pump programming.

Referring now to FIG. 5, by lowering the barriers to the preparation of programs for pumps 12, each given application program 38 may be greatly simplified to implement a single specialized procedure or a limited number of procedures 86 less than the full range of procedures of which the pump 10 is capable. Rather than constructing a single application program that can perform all features, an equivalent range of use of the pump 10 is obtained by using multiple application programs 38. The benefit is that each application program 38 is much easier to use and that a pump 10 may contain only a few application programs relevant 38 for particular use context.

In this case, the application program 38 may have a preset data table 88, for example, providing expert settings for that particular procedure associated with the application program 38. These default settings are possible because of the narrow focus of the application program 38. Thus, for example, a display 90 of the pump 10 (or of a remote device as will be discussed below) may provide a very simple hierarchy showing each of a limited number of procedures 86 that the pump 10 can implement. Each procedure 86 may be a different application program 38 or a single application program 38 nevertheless limited in purpose.

Because the procedures 86 have narrow focus, settings 92 for each procedure may be predetermined by the programmer and may be automatically loaded from the preset data table 88 when the procedure 86 is invoked. In one option, these settings 92 may be displayed in a table on the display 90 that is pre-populated with recommended values for the procedure and yet which allows adjustment by the user if desired. It is anticipated that in many cases most settings 92 of the pump 10 for the given procedure 86 can be used as presented. Some settings will be specific to the patient, for example, patient specific data such as weight, but these may be quickly entered.

Figure 6:
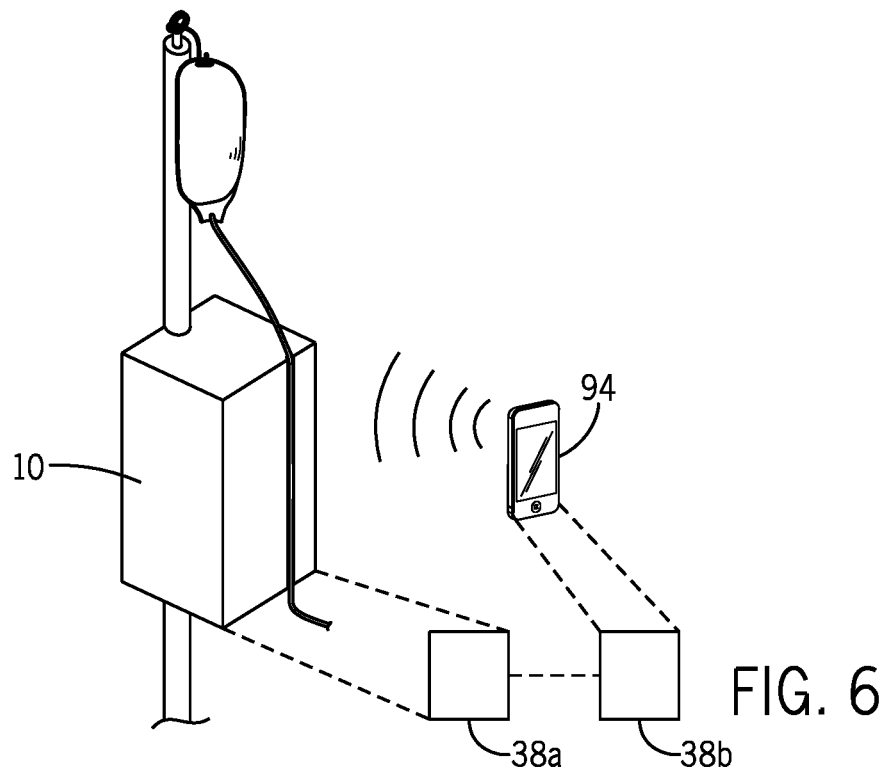
FIG. 6 is a view of a pump and remote computational device such as a cell phone showing an ability to divide the functions required by an application program between a pump and an external device.

Referring to FIGS. 2 and 6, as discussed above with respect to FIG. 2, not all pumps 12 will necessarily have a sophisticated user interface and accordingly the invention defines a remote object (57 shown in FIG. 2) that encapsulates the programming needed to communicate with a remote interface device 94 such as a cell phone, tablet, laptop, or desktop computer whose resources will thereby be available to the application program 38. Using the remote object 57, user input and output features may be delegated to the remote device 24 rather than the pump 10 by splitting the application program 38 into portions 38*a* associate with the pump 10 and portion 38*b* associated with the remote interface device 84 automatically connected together by communication protocols implemented by the remote object 57.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A system of medical pumps comprising:
at least two pumps, each pump having
a housing;
multiple hardware elements that differ between pumps including:
(i) an electrical pump for receiving a line controlling a flow of liquid medicament therethrough;
(ii) one or more sensors for sensing pump and/or line conditions; and
(iii) an electronic user interface providing a display and keyboard;
an electronic memory holding an operating system, an application loader program, and a standardized interface of the operating system including task programs implementing standard control of the multiple different hardware elements of the at least two pumps; and
an electronic computer communicating with the hardware elements of the at least two pumps and the electronic memory and executing the operating system and the application loader program to:
(1) receive multiple third party application programs of executable instructions for separately loading into the electronic memory and load the multiple application programs into the electronic memory only if the multiple application programs include embedded authentication data indicating that the application program is certified to operate the pump correctly for medical use, and if not, locking out the application program from executing;
(2) display representations of the multiple application programs in a hierarchical menu structure on the display of the at least two pumps for executing by user input to the keyboard of the at least two pumps to select between the multiple application programs, each application program independently operable to control the medical pump for patient treatment; and (3) execute the multiple application programs to communicate through the operating system to the hardware elements of the at least two pumps, the standardized interface of the operating system providing identical abstractions of the different hardware elements of the at least two pumps so that the same executable instructions are executable on the multiple different hardware elements of the at least two pumps wherein the standardized interface includes a standard session interface exchanging information between the multiple application programs and the hardware elements to coordinate among a pump and at least one sensor for sensing fluid flow to provide a patient treatment session for an individual patient, the standard session interface accepting values from an application program of at least one of flow rate and flow volume for medicament delivery and including a standard error event exchanging information between an application program and the hardware elements to coordinate a stopping of the pump in the event of a predetermined error condition related to the flow of medicament determined by a sensor.

2. The medical pump of claim 1 wherein the embedded authentication data is a digital signature.

3. The medical pump of claim 1 further including a wireless receiver and wherein the application loader program receives application programs wirelessly.

4. The medical pump of claim 1 wherein the application loader program compares the standardized interface used by the application program to standardize interfaces available on the medical pump before receiving an application program.

5. The medical pump of claim 1 wherein the standardized interface provides a plurality of software objects associated with the hardware elements, the software objects providing object properties having values describing operation of the hardware elements, object methods having sequences of steps for controlling the hardware elements, and object events having test conditions receiving information from the hardware elements to trigger outputs to the application programs.

6. The medical pump of claim 5 wherein the software objects include: a pump object, at least one sensor object, a data logging object, a display object, a keyboard object and an error object.

7. The medical pump of claim 6 wherein the data logger object records a digital signature of the application program.

8. The medical pump of claim 5 wherein the software objects include a session object coordinating the electrical pump and the one or more sensors according to a timer.

9. The medical pump of claim 1 wherein the standardized interface limits the operating conditions of associated hardware elements independently of data received by the application programs.

10. The medical pump of claim 1 wherein the application loader program further operates to remove one or more application programs from the electronic memory.

11. A method of managing a set of infusion pumps having different hardware elements comprising:

(a) generating a set of pump control application programs of executable instructions using a development program for generating output for communicating with a standardized interface including task programs implementing standard control of multiple different hardware elements of the set of infusion pumps and identical abstractions of the different hardware elements of the set of infusion pumps so that the same executable instructions are executable on the multiple different hardware elements of the set of infusion pumps;

(b) loading each infusion pump with an operating program translating executable instructions communicated to the standardized interfaces to standard control instructions of specific hardware elements on the infusion pumps;

(c) loading each infusion pump with selected multiple pump control application programs; and (d) presenting the selected multiple pump control application programs in a menu to a user allowing the user to execute identified ones of the selected multiple pump control application programs for control of each infusion pump wherein the application programs include multiple third party application programs and are displayed in a hierarchical menu structure on the display;

wherein the application loader program operates to separately load application programs into the electronic memory only if the application programs include embedded authentication data indicating that the application program is certified to operate the pump correctly for medical use, and if not, locking out the application program from executing; and wherein the standardized interface includes a standard session interface exchanging information between the application program and the hardware elements to coordinate among a pump and at least one sensor for sensing fluid flow to provide a patient treatment session for an individual patient, the standard session interface accepts values from an application program of at least one of flow rate and flow volume for medicament delivery and includes a standard error event exchanging information between an application program and the hardware elements to coordinate a stopping of the pump in the event of a predetermined error condition related to the flow of medicament determined by a sensor.

12. The method of claim 11 wherein the standardized interface include a standard session interface coordinating a pump, timer, and at least one fluid sensor to provide a medicament delivery session for an individual patient.

* * * * *